United States Patent
Fujita et al.

(10) Patent No.: US 9,448,244 B2
(45) Date of Patent: Sep. 20, 2016

(54) COMPOUND, AND METHOD FOR MEASURING IRON CONCENTRATION BY USING NOVEL COMPOUND AS CHELATE COLOR FORMER

(71) Applicant: WAKO PURE CHEMICAL INDUSTRIES, LTD., Osaka-shi, Osaka (JP)

(72) Inventors: Yoshikazu Fujita, Takatsuki (JP); Toshinari Ohashi, Amagasaki (JP); Naoyuki Yamamoto, Amagasaki (JP); Takashi Takagaki, Amagasaki (JP); Satoshi Hasaba, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 14/433,311

(22) PCT Filed: Oct. 15, 2013

(86) PCT No.: PCT/JP2013/077880
§ 371 (c)(1),
(2) Date: Apr. 2, 2015

(87) PCT Pub. No.: WO2014/061623
PCT Pub. Date: Apr. 24, 2014

(65) Prior Publication Data
US 2015/0260734 A1   Sep. 17, 2015

(30) Foreign Application Priority Data

Oct. 17, 2012   (JP) .................. 2012-230140

(51) Int. Cl.
| | |
|---|---|
| *C09B 11/28* | (2006.01) |
| *G01N 33/20* | (2006.01) |
| *G01N 33/84* | (2006.01) |
| *C09B 11/24* | (2006.01) |
| *G01N 31/00* | (2006.01) |
| *C09B 49/12* | (2006.01) |
| *G01N 33/90* | (2006.01) |
| *G01N 31/22* | (2006.01) |

(52) U.S. Cl.
CPC ............... *G01N 33/84* (2013.01); *C09B 11/24* (2013.01); *C09B 11/28* (2013.01); *C09B 49/12* (2013.01); *G01N 31/00* (2013.01); *G01N 33/20* (2013.01); *G01N 31/22* (2013.01); *G01N 33/90* (2013.01)

(58) Field of Classification Search
CPC ....... G01N 33/20; G01N 33/90; C09B 11/28
See application file for complete search history.

(56) References Cited

FOREIGN PATENT DOCUMENTS

WO   2004040252   5/2004

OTHER PUBLICATIONS

Hoshino et al.: "Improved Spectrophotomeric Determination of Total Iron and Iron(III) with o-Hydroxyhydroquinonephthalein and Their Characterization"; Yakugaku Zasshi, vol. 131, No. 7 (2011), pp. 1095-1101.
Marczenko et al.: "Separation, Preconcentration and Spectrophotometry in Inorganic Analysis"; Analytical Spectroscopy Library, vol. 10 (2000), pp. 59-60.
Fujita et al.: "Spectrophotometric Determination of Ascorbic Acid with Iron(III) and p-Carboxyphenylfluorone in a Cationic Surfactant Micellar Medium"; Analytical Sciences, vol. 17 (2001), pp. 853-857.
International Search Report, Nov. 26, 2013; PCT/JP2013/077880 (1 page).
K. Gu et al., "Spectrophotometric Determination of Iron in Caprolactam with 2,4-Diiodine phenylflorone," Journal of Yunnan University (Nature Science Edition), 1999, vol. 21(4), p. 305-306 (6 pages including English translation).
DA Tsybulsky et al., "4',5'-Dichloro-2',7'-dimethoxy-5(6)-carboxyfluorescein (JOE): Synthesis and Spectral Properties of Oligonucleotide Conjugates," The Journal of Organic Chemistry, 2012, v. 77, p. 977-984.
Extended European Search Report for European Application No. 13846619.8, dated May 12, 2016, 10 pages.

*Primary Examiner* — Paul Hyun
(74) *Attorney, Agent, or Firm* — Hamre, Schumann, Mueller & Larson, P.C.

(57) ABSTRACT

The present invention addresses the problem of providing a chelate color former which can measure the concentration of iron with high sensitivity and with low blank values when measuring the concentration of iron, and an iron concentration measurement method and kit that use this chelate color former. The present invention relates to: a compound represented by following formula [1] or a salt thereof

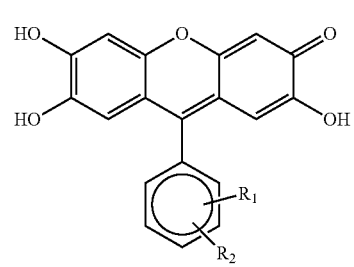

[1]

wherein, $R_1$ and $R_2$ each independently represent $-SO_3H$ or $-CO_2H$; an iron concentration measurement method in which the compound is used as a chelate color former, the compound is brought into contact with iron in a sample, and the concentration of iron in the sample is measured on the basis of the degree of resulting color development; and a kit to be used therein.

2 Claims, 4 Drawing Sheets

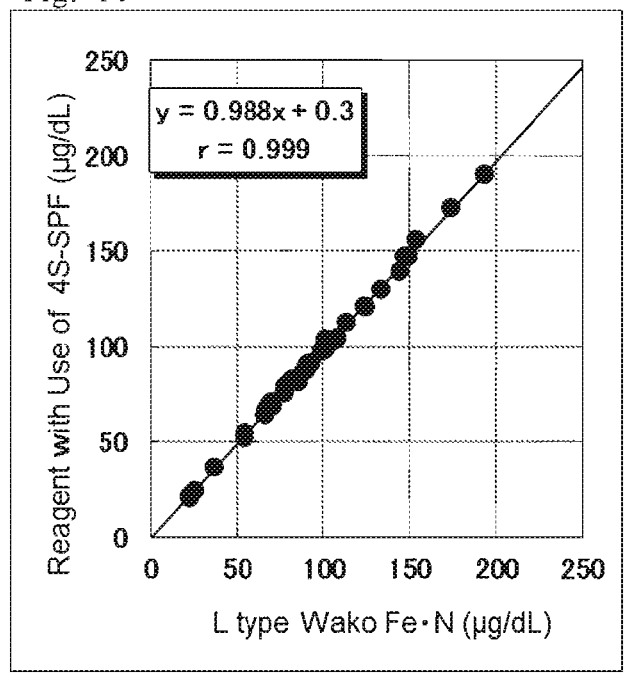

COMPOUND, AND METHOD FOR MEASURING IRON CONCENTRATION BY USING NOVEL COMPOUND AS CHELATE COLOR FORMER

TECHNICAL FIELD

The present invention relates to a novel compound and a method for measuring iron concentration in a sample using this compound as a chelate color former.

BACKGROUND ART

Measurement of iron concentration in serum and plasma has been utilized for the diagnosis of anemia, hypoferric anemia, hepatic cirrhosis and the like, and is one of important measurement items in the field of clinical laboratory test.

As the method for measuring iron concentration, for example, colorimetric analysis using various metal chelate color formers such as dipyridyl, o-phenanthroline has been employed commonly, and iron chelate color formers such as sodium bathophenanthroline sulfonate, 2-nitroso-5-(N-propyl-N-sulfopropylamino)-phenol (nitroso PSAP), 3-(2-pyridyl)-5,6-bis[2-(5-furylsulfonic acid)]1,2,4-triazine disodium salt, tripyridyltriazine, ferrozine have been used as a color former.

Since all of these iron chelate color formers develop a color by forming a chelate with divalent iron, on the occasion of using, these require to be used in combination with a reducing agent for the reduction of trivalent iron. As the reducing agent of trivalent iron, L-ascorbic acid, thioglycolic acid, hydroxylamine hydrochloride, hydroquinone, hydrosulfite, sodium sulfite, hydrazine sulfate, metabisulfite (pyrosulfite) and the like have been known.

However, since these reducing agents degrade during storage, the reagents for measuring iron concentration which have been used conventionally had a problem in storage stability of the reagent.

And so, the present inventors have developed a compound represented by the following formula [A] (9-(2-carboxyphenyl)-2,3,7-trihydroxy-6-fluorone, hereinafter abbreviated as CPF) as a dye which reacts with both the trivalent iron and divalent iron (Non-Patent Literature 1).

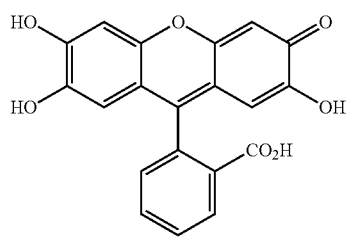

[A]

CITATION LIST

Non-Patent Literature

Non-Patent Literature 1: Mitsuru Hoshino et al., Yakugaku Zassi, 2011, vol. 131, No. 7, p. 1095-1101.

SUMMARY OF INVENTION

Technical Problem

When the iron concentration is measured using CPF as an iron chelate color former, there is an advantage that the use of reducing agent which has a problem in storage stability of the reagent is not needed. However, on the other hand, there was a problem that the blank value of the measurement is increased.

The present invention has been made in view of such situation, and has an object to provide a chelate color former which can measure the concentration of iron with high sensitivity and with low blank value, and a method for measuring iron concentration and a kit using therefor.

Solution to Problem

The present invention has been made for the purpose of solving the above-described problems, and comprises the following aspects:

(1) A compound represented by the following formula [1] or a salt thereof:

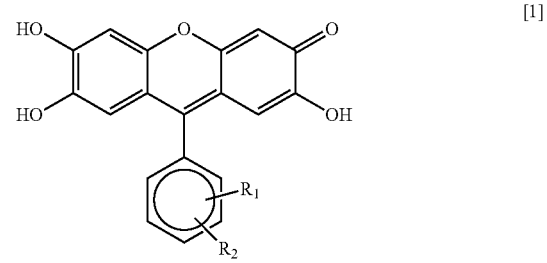

[1]

wherein, $R_1$ and $R_2$ each independently represent —$SO_3H$ or —$CO_2H$.

(Hereinafter, when a compound is described as "compound represented by the formula [1]", it may sometimes include a compound represented by the formula [1] and the salt thereof.).

(2) A method for measuring iron concentration in a sample, comprising contacting an iron in the sample with an compound represented by the following formula [1] or the salt thereof as a chelate color former, measuring iron concentration in a sample on the basis of a degree of resulting color development.

(3) A kit for measuring iron concentration comprising a compound represented by the formula [1] or the salt thereof as a constituent reagent.

That is, the present inventors have studied intensively to solve the above-described problems, and as a result, the present inventors have synthesized a novel compound represented by the above-described formula [1]. And, the compound was found to be excellent in color development at the time of forming a chelate with iron, and also to be high in water solubility. Further, it was found that when the measurement of iron concentration is performed by using the compound represented by the formula [1] as a chelate color former, the iron concentration can be measured with high sensitivity, and have thus accomplished the present invention.

Advantageous Effects of Invention

The present invention provides a novel compound represented by the formula [1]. When the compound is used as a chelate color former, the measurement of iron concentration in a sample can be performed without using a reducing agent. Moreover, since the reagent blank value becomes lower than that of the conventionally used CPF, and the color of a chelate with iron is stable without fading, the measurement of iron concentration can be performed with high sensitivity and with high accuracy than that performed conventionally. Further, the compound reacts with both divalent iron and trivalent iron to constitute a chelate. Therefore, the reagent and the kit for measuring iron concentration which comprise the compound as a constituent are excellent in the storage stability because inclusion of the reducing agent is not required, in addition, the present invention may bring about an effect that the compound provides a good usability as a reagent due to its high solubility in water.

BRIEF DESCRIPTION OF DRAWINGS

FIG. 10 is a correlation diagram between the serum iron concentration measurements obtained by using 4S-SPF as a chelate color former and that obtained by using bathophenanthroline which is the conventionally used chelate color former, obtained in Example 6.

DESCRIPTION OF EMBODIMENTS

Figure 1:
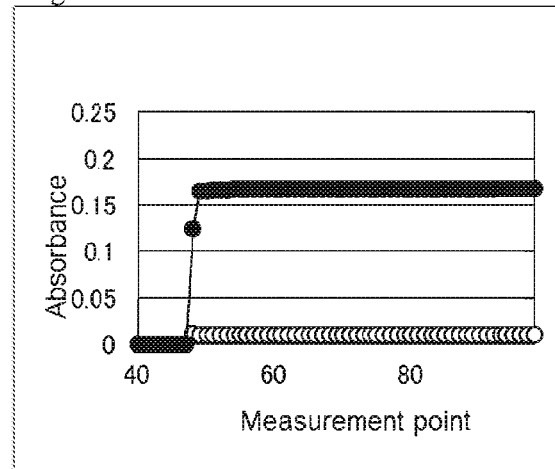
FIG. 1 is the measurement results of absorbance carried out using 9-(2,4-disulfophenyl)-2,3,7-trihydroxy-6-fluorone (4S-SPF) as a chelate color former, obtained in Example 3.

In the compound represented by formula [1] of the present invention, it is preferable that $R_1$ is located in the ortho position with respect to the binding position of xanthene skeleton, and $R_2$ is located in the para position with respect to the binding position of xanthene skeleton. That is, the compound represented by the following formula [B] or the salt thereof is more preferable.

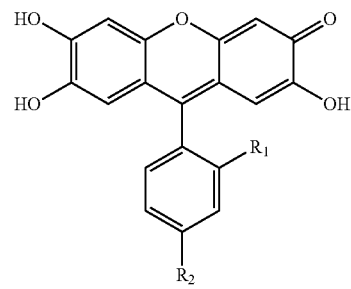

[B]

wherein, $R_1$ and $R_2$ each independently represent —$SO_3H$ or —$CO_2H$.

Wherein formula [1], it is preferable that at least one of $R_1$ and $R_2$ is —$SO_3H$.

The salt of the compound represented by the formula [1] of the present invention includes, for example, an alkali metal salt such as sodium salt and potassium salt, an alkali earth metal salt such as calcium salt and magnesium salt, an organic amine salt such as ammonium salt, triethylamine salt and dimethylamine salt, and the like. Sodium salt and potassium salt are particularly preferable.

The compound represented by the formula [1] of the present invention includes, for example, 9-(2,4-disulfophenyl)-2,3,7-trihydroxy-6-fluorone represented by the following formula [2] (in the formula [B], the compound of $R_1$=$SO_3H$ and $R_2$=$SO_3H$, hereinafter abbreviated as 4S-SPF.) or the salt thereof, or

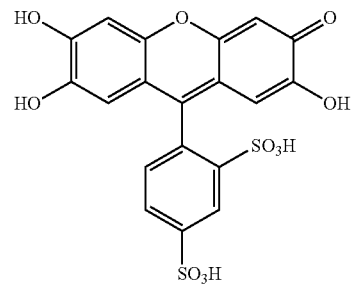

[2]

9-(4-carboxy-2-sulfophenyl)-2,3,7-trihydroxy-6-fluorone represented by the following formula [3] (in the formula [B], the compound of $R_1$=$SO_3H$ and $R_2$=COOH, hereinafter abbreviated as 2S-4CPF) or the salt thereof, and the like.

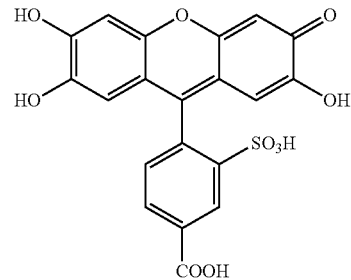

[3]

The compound represented by the formula [1] of the present invention can be synthesized, for example, according to the following synthetic route.

4S-SPF can be synthesized, for example, according to the following synthetic route (synthetic route A).

[Synthetic Route A]

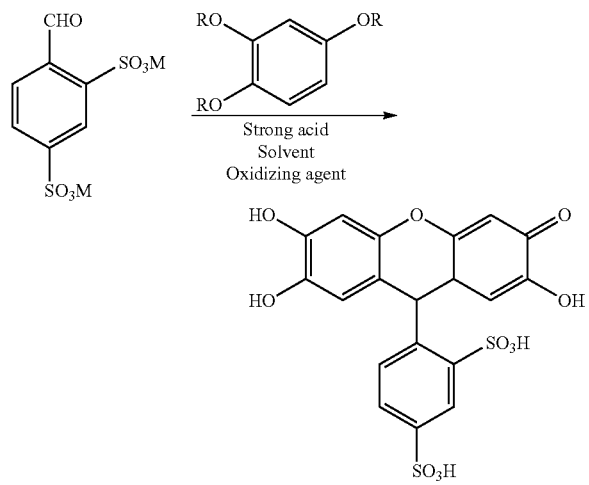

The type of counter cation represented by NI of the sulfonic acid to be used in the synthetic route A is not particularly limited, and there are included alkali metal salts such as sodium salt and potassium salt, alkali earth metal salts such as calcium salt and magnesium salt, organic amine salts such as ammonium salt, triethylamine salt, dimethylamine salt and the like. A sodium salt and a potassium salt are particularly preferable.

The R of 1,3,4-benzotriol to be used in the synthetic route A includes a hydrogen atom and acyl type protecting group such as an acetyl group, a pivaloyl group, a benzoyl group. Particularly, a hydrogen atom or an acetyl group is preferable.

The strong acid to be used in the synthetic route A includes sulfuric acid, hydrogen chloride, hydrogen bromide, nitric acid, perchloric acid, hydrogen iodide, and the like. Particularly, sulfuric acid or hydrogen chloride is preferable.

The solvent to be used in the synthetic route A includes lower alcohols such as methanol, ethanol, isopropanol, ethylene glycol, glycerin, higher alcohols (having 6 or more of carbon number and not containing unsaturated bond) such as capryl alcohol, lauryl alcohol, myristyl alcohol, cetyl alcohol, stearyl alcohol. Particularly, ethanol or isopropanol is preferable.

The oxidizing agent to be used in the synthetic route A includes persulfate salts which easily generate free radical in solution and have a strong oxidizing action. For example, there are included potassium persulfate (KPS), ammonium persulfate (APS) and sodium persulfate (NPS), and potassium persulfate (KPS) is particularly preferable.

As a specific synthetic method of 4S-SPF, for example, 2,4-disulfonic acid benzaldehyde and 1,3,4-benzotriol (2 to 10 times mol to 2,4-disulfonic acid benzaldehyde) are heated at about 40° C. to 180° C. in the presence of an appropriate amount of the above-described strong acid and the solvent, then without purifying intermediate products, heated at about 40° C. to 180° C. in the presence of the above-described oxidizing agent, thereby the 4S-SPF can be synthesized. After completion of the reaction, by using a solvent in which the solubility of an objective substance is low, for example, using the solvent such as ethanol, methanol, isopropanol, butanol, acetonitrile and acetone, unreacted reagents, other solvents, raw material reagents, impurities, etc. can be removed. By carrying out purification in this way, the objective compound can be obtained.

2S-4CPF can be synthesized, for example, according to the following synthetic route (synthetic route B).

[Synthetic Route B]

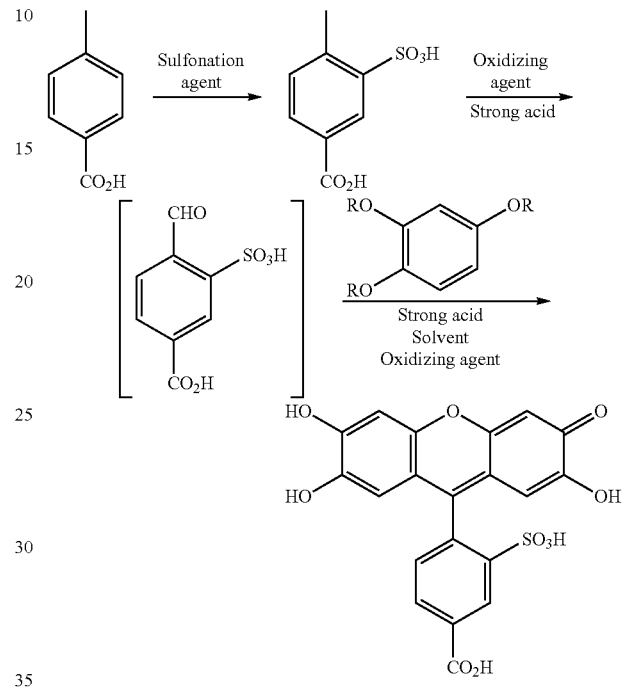

The sulfonating agent to be used in the synthetic route B includes the reagents which introduce a sulfo group through electrophilic substitution reaction, such as chlorosulfuric acid, fuming sulfuric acid and sulfuric acid, and chlorosulfuric acid is particularly preferable.

In the synthesis route B, the oxidizing agent for converting from a methyl group to an aldehyde group includes manganese oxide, manganese sulfate, etc.

The R of 1,3,4-benzotriol to be used in the synthetic route B includes hydrogen atom, or an acyl type protecting group such as an acetyl group, a pivaloyl group, a benzoyl group and the like. Particularly, hydrogen atom or an acetyl group is preferable.

The strong acid to be used in the synthetic route B includes sulfuric acid, hydrogen chloride, hydrogen bromide, nitric acid, perchloric acid, hydrogen iodide and the like, and sulfuric acid or hydrogen chloride is particularly preferable.

The solvent to be used in the synthetic route B includes lower alcohols such as methanol, ethanol, isopropanol, ethylene glycol, glycerin, etc., higher alcohols (having 6 or more of carbon number and not containing unsaturated bond) such as capryl alcohol, lauryl alcohol, myristyl alcohol, cetyl alcohol, stearyl alcohol, etc., and ethanol is particularly preferable.

In the synthetic route B, the oxidizing agent to be used to convert the aldehyde body to an objective substance includes persulfate salts which easily generate free radical in solution and have a strong oxidizing action. For example, there are included potassium persulfate (KPS), ammonium persulfate (APS) and sodium persulfate (NPS), and potassium persulfate (KPS) is particularly preferable.

A specific synthetic method of 2S-4CPF includes the following method. First, p-toluic acid is heated at about 0° C. to 95° C. in the presence of sulfonat ng agent (2 to 10 times mol amount to p-toluic acid), and the resultant compound is purified with a normal phase column or a reverse phase column. Then, the resultant compound is heated at about 0° C. to 120° C. in the presence of the above-described oxidizing agent (5 to 20 times mol: amounts to the resultant compound) and excess amount of strong acid to produce the aldehyde body. Further, without purifying the aldehyde body, 3,4-benzotriol (2 to 10 times mol to 4-methyl-3-sulfobenzoic acid) is added, and reacted by heating at about 0° C. to 90° C. in the presence of appropriate amount of the above-described strong acid and solvent. Then, the resultant reaction product is heated at about 0° C. to 90° C. in the presence of the above-described oxidizing agent (1 to 10 times mol to 4-methyl-3-sulfobenzoic acid), and reacted, thereby the objective 2S-4CPF is obtained. In order to purify the resultant 2S-4CPF, further, by using a solvent having the low solubility of 2S-4CPF, for example, ethanol, methanol, isopropanol, butanol, acetonitrile and acetone, etc. unreacted reagents, other solvents, raw material reagents, impurities, etc. may be removed.

The method for measuring iron concentration of the present invention is "a method for measuring iron concentration in a sample, comprising contacting an iron in the sample with an compound represented by the following formula [1] or the salt thereof as a chelate color former, measuring iron concentration in a sample on the basis of a degree of resulting color development".

Specific examples of the compound represented by the formula [1] to be used in the method for measuring iron concentration of the present invention are as described above. As the chelate color former to be used in the method for measuring iron concentration, 2S-4CPF or 4S-SPF is preferable.

The usage of the chelate color former pertaining to the present invention is not particularly limited, and may be determined in accordance with the characteristics of the chelate color former, however, for example, the concentration in the reagent solution comprising the chelate color former is 0.5 to 5 mM, preferably 0.5 to 2 mM, and the final concentration in the reaction solution at the time of measuring iron concentration is 0.1 to 1 mM, preferably 0.2 to 0.5 mM.

In order to perform the method for measuring iron concentration of the present invention, except for the use of the chelate color former of the present invention, the method for measuring iron concentration by the direct measurement method well-known per se, the international standard methods, or Matsubara's modified method of the international standard method may be carried out. And, measurement conditions (for example, reaction time, measuring wavelength, etc.) and measurement procedure may also be carried out according to the method well-known per se.

In the method for measuring iron concentration of the present invention, the method for bringing the chelate color former of the present invention into contact with iron in a sample may be any method for obtaining finally a solution which contains the sample and the chelate color former of the present invention.

The specific method includes, for example, the following methods:

(1) A method in which a solution comprising buffering agents (first reagent solution) and a solution containing the chelate color former of the present invention (second reagent solution are prepared in advance, and the first reagent solution and the second reagent solution are added to the sample in this order, (2) A method in which a solution comprising the chelate color former of the present invention is prepared and the solution is added to the sample.

Considering the case where the measurement is carried out using an automated analyzer, the method of (1) (two reagent solutions method) is a common and preferable.

As the solution for dissolving the chelate color former of the present invention, since it is desirable to perform the measurement of iron concentration in the optimal pH range of the chelate color former, a buffer solution is preferable.

In the method for measuring iron concentration of the present invention, the preferable pH of the final reaction solution at the time of measurement of iron concentration is pH 6 to 10, and more preferably it is pH 6 to 9. As the buffering agent constituting buffer solution to be used for providing the above-described pH range, any buffering agents which are usually used in this field can be used. Specifically, there are included, for example, Good's buffering agent such as tricine and bicin, glycine, acetic acid, citric acid, tartaric acid and the like.

Further, in the solution containing the chelate color former of the present invention, in addition to these reagents, the substances, which are usually used in this field, such as preservatives, stabilizers, reaction accelerators and ion concentration adjusters may be allowed to coexist.

As for these reagents, it is desirable to select the one which is highly stable within the optimal pH rage of the chelate color former of the present invention and which does not inhibit color development of the chelate color former of the present invention. In addition, the concentration ranges of these reagents are also sufficient to be used by the appropriate selection of the concentration range commonly used in the measurement method well-known per se.

In addition, a surfactant may be contained in the solution containing the chelate color former to be used in the measurement method of the present invention, the first reagent solution and the second reagent solution in the above-described two reagent solution method.

Such surfactant is not particularly limited as long as it is the surfactant usually used in this field and it does not inhibit color development of the chelate color former of the present invention, and specifically, includes, for example, polyvinyl pyrrolidones, polyoxyethylene alkyl ethers such as polyoxyethylene cetyl ether, polyoxyethylene lauryl ether, for example, polyoxyethylene alkyl phenyl ethers such as polyoxyethylene octyl phenyl ether, for example, polyoxyethylene alkyl esters such as polyoxyethylene sorbitan monooleate, polyoxyethylene sorbitan monolaurate, polyoxyethylene sorbitan monopalmitate, polyoxyethylene sorbitan monostearate, polyoxyethylene sorbitan trioleate, for example, methylglucamide derivative such as octanoyl-N-methylglucamide, nonanoyl-N-methylglucamide, decanoyl-N-methylglucamide, for example, non-ionic surfactant such as the alkyl sugar derivative such as n-octyl-β-D-glucoside, for example, anionic surfactant such as sodium dodecyl sulfate (SDS), lauryl benzenesulfonic acid, deoxycholic acid, cholic acid, Tris(hydroxymethyl) aminomethane dodecyl sulfate (Iris DS), for example, alkyl amine salt such as octadecylamine acetate, tetradecylamine acetate, stearylamine acetate, lauryl amine acetate, lauryl diethanolamine acetate, for example, quaternary ammonium salt such as octadecyl trimethyl ammonium chloride, dodecyl trimethyl ammonium chloride, cetyl trimethyl ammonium chloride, cetyl trimethyl ammonium bromide, lauryl trimethyl ammonium chloride, allyl trimethyl ammonium methylsulfate, benzalkonium chloride, tetradecyl dimethyl benzyl ammonium chloride, octadecyl dimethyl benzyl ammonium chloride, lauryl dimethyl benzyl ammonium chloride, for example, cationic surfactant such as alkyl pyridinium salt such as lauryl pyridinium chloride, stearylamide methylpyridinium chloride, and amphoteric surfactant such as sodium lauroylmethyl-β-alanine, 3-[(3-Cholamide amidopropyl)dimethylammonio]-1-propanesulfonate, 3-[(3-Cholamide amidopropyl)dimethylammonio]-2-hydroxy-1-propanesulfonate, and the like. Further, these may be used alone or may be used appropriately in combination of two or more thereof.

The concentration in use of the above-described surfactant may be selected appropriately from a range commonly used in this field. The concentration of the above-described surfactant in the solution comprising the chelate color former of the present invention, in the first reagent solution and/or second reagent solution in the two reagent solution method is usually about 0.0001% to 10% (W/V), preferably about 0.001% to 5% (W/V), and the concentration in the final reaction solution is usually about 0.001% to 10% (W/V), preferably about 0.01% to 5% (W/V).

After allowed to react the chelate color former of the present invention with the sample, the absorbance change due to color development of the chelate color former may be measured according to the method for measuring iron concentration such as direct methods well-known per se. The automated analyzer, spectrophotometer, etc. to be used in the measurement, any equipment usually used in this field can be used without exception. In addition, it goes without saying that the absorbance change may be measured by two-wavelength photometry using dominant wavelength and secondary wavelength.

When the absorbance measurement is performed by two wavelengths, the wavelength for the absorbance measurement may be selected appropriately around the maximum absorption wavelength of the chelate color former of the present invention to be used in accordance with the set wavelength of the equipment used for the measurement. When a general-purpose automated analyzer for the determination of serum iron concentration is used, the measurement may be performed usually with dominant wavelength at around 600 nm and secondary wavelength at around 700 nm.

The sample to be used in the methods of the present invention includes, for example, biogenical components such as urine, serum, plasma.

In the conventional method for measuring iron concentration, since the color former which develops color by forming a chelate with divalent iron is used, the trivalent iron that is bound to transferrin in the sample is required to be liberated and reduced to the divalent iron. Therefore, the reducing agent has been used.

However, in the method for measuring iron concentration of the present invention, since the compound represented by formula [1] of the present invention for use in the measurement reacts with both divalent iron and trivalent iron, the reducing agent need not be used.

It should be noted that, if the chelate color former of the present invention is used, it is possible to measure iron concentration in the sample in the absence of reducing agent, but even if the measurement is carried out in the presence of the reducing agent, it does not affect the measurement.

Taking the above-described method (1) (the method in which a solution comprising the buffering agents (first reagent solution) and a solution comprising the chelate color former of the present invention (second reagent solution) are prepared, then the first age solution and the second reagent solution are added to the sample in this order) as an example, the method for measuring iron concentration of the present invention is described more specifically, for example, as follows.

First, for example, a san p e to be measured for iron concentration is mixed with the first reagent solution comprising the buffering agents (pH 3 to pH 9, when the sample is a sample derived from living organism such as serum, it is pH 3 to pH 7), and reacted usually at 10° C. to 50° C., preferably at 20° C. to 40° C., usually for 2 minutes to 10 minutes, preferably for about 5 minutes. Then, the reaction solution is mixed with the second reagent solution comprising the chelate color former of the present invention (pH 7 to pH 10), and reacted usually at 10° C. to 50° C., preferably at 20° C. to 40° C., usually for 2 minutes to 10 minutes, preferably for about 5 minutes. Then, the color development caused by the reaction of the chelate color former of the present invention and iron in the sample is measured as absorbance. By applying the obtained measurement value to a standard curve showing the relationship between the absorbance and the iron concentration, which was prepared, for example, by performing the measurement in the same manner using a sample of standard iron solution of known concentration in advance, the iron concentration in the sample is measured.

The above-described measurement of iron concentration may be performed by a manual means as a matter of course, it goes without saying that it may be performed using an automated analyzer. It should be noted that, the combination of the reagents in the case of performing measurement by a manual menans or using an automated analyzer is not particularly limited, and may be performed appropriately in accordance with the environment of the automated analyzer applied and other factors.

A kit for measuring iron concentration of the present invention may be the one which is comprised of a reagent including the chelate color former of the present invention as a constituent reagent. Preferred embodiment of respective constituent, specific example and the concentration to be used, etc. are as described above.

Specific embodiment of the kit of the present invention may be those prepared for the single reagent solution (reagent) system measurement or the two reagent solution (reagent) system measurement, and those are not particularly limited. For example, the following constitutions are included:

(1') the one which is consisted of the first reagent solution comprising the buffering agent and the second reagent solution comprising the chelate color former of the present invention; or (2') the one in which a solution comprising the chelate color former of the present invention is a constituent reagent.

In addition, in a specific embodiment of the above-described kit of the present invention, the concentration of the chelate color former of the present invention in the reagent solution comprising the chelate color former which constitutes a kit for the single reagent system measurement method or a kit for the two reagent solution system measurement method is 0.5 mM to 5 mM, preferably 0.5 mM to 2 mM.

The pH of the chelate color former of the present invention constituting the kit is pH 3 to pH 10, preferably pH 6 to pH 10. When the kit is consisted of the first reagent solution comprising the above-described buffering agent and the second reagent solution comprising the chelate color former of the present invention, it is preferable that the pH of the first reagent solution comprising the above-described buffering agent is pH 3 to pH 9, and the pH of the second reagent solution comprising the chelate color former of the present invention is pH 7 to pH 10. In addition, in the case of the kit to be used when the sample derived from a living organism such as serum is used as a reagent sample and the measurement is carried out by the two reagent solution system measurement, as mentioned above, the pH of the first reagent solution is pH 3 to pH 7, preferably pH 3 to pH 6.

In addition, in each reagent of the kit, there may be contained the substances which are usually used in this field, for example, surfactants, buffering agents, preservatives, stabilizers, reaction accelerators, etc. in the range usually used in this field. Specific examples thereof are as described in the explanation of the method for measuring iron concentration of the present invention. Further, it may contain a protein denaturant to liberate iron from transferrin, or imidazole or the like, in order to avoid the influence on the measurement value when a hemolyzed sample is measured.

For example, when the kit is prepared for the two reagent solution system measurement, other than the buffering agents and pH regulator, the above-described surfactants, reaction accelerators such as organic acids and ion concentration regulators may be included in the first reagent solution. In addition, in the case of a kit for measuring iron concentration in a sample derived from living organism such as serum, a protein denaturing agent to liberate iron from transferrin may be contained in the first reagent solution. In addition, the buffering agents and pH regulators, the stabilizer of the chelate color former of the present invention may be contained in the second reagent solution. Further, the first reagent solution or the second reagent solution may contain imidazole or the like in order to avoid the influence on the measurement value when a hemolyzed sample is measured.

In addition, the kit need not contain the reducing agent as a constituent, however, since the reducing agent does not effect on the method for measuring iron concentration of the present invention, there is no problem even the kit contains the reducing agent.

It should be noted that, when the kit is composed of plural reagent solutions as described in (1) above, these reagents may be dispersed and contained appropriately in either of these reagent solutions so that the reaction for the measurement of the analyte is starts when each reagent solution is mixed. The concentrations in use of the reagents for constituting these reagent solutions may be selected as appropriate from the ranges usually used in this field.

Further, the kit may be combined with an iron standard as needed.

Hereinafter, the present invention will be further explained in detail by referring to the following Examples and Comparative Examples, by the scope of the present invention should not be limited thereto.

EXAMPLES

Example 1

Synthesis of 9-(2,4-disulfophenyl)-2,3,7-trihydroxy-6-fluorone (the compound of formula [B], wherein $R_1=SO_3H$, $R_2=SO_3H$, hereinafter described as 4S-SPF)

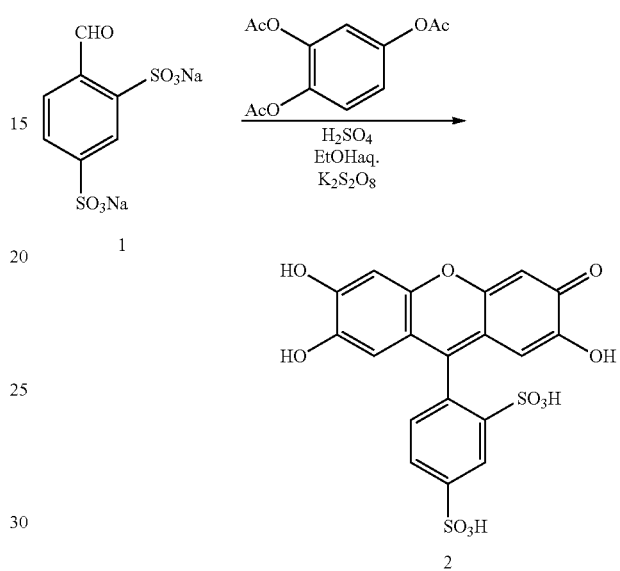

Benzaldehyde-2,4-disulfonic acid disodium (1) (5.0 g, 0.016 mol, produced by Wako Pure Chemical Industries, Ltd.) and 1,3,4-triacetoxybenzene (8.2 g, 0.032 mol, produced by Wako Pure Chemical Industries, Ltd.) were subjected to Friedel-Crafts acylation reaction at 80° C. using concentrated sulfuric acid (10 mL) and 50% ethanol (200 mL) as the solvent. After confirming the disappearance of the starting materials by HPLC, further by adding potassium persulfate (4.4 g), oxidative ring closure reaction was carried out at 80° C. After completion of the reaction, the reaction mixture was allowed to stand overnight. Precipitated crystals were washed with cooled 50% ethanol to obtain the objective 4S-SPF (2) (yield: 5.98 g, yield: 77%)

$^1$H-NMR (DMSO-$d_6$) δ (ppm): 6.69 (2H, s), 7.15 (1H, d), 7.26 (2H, s), 7.76 (1H, d), 8.27 (1H, s).

MALDI TOP Mass (posi: 481).

Example 2

Synthesis of 2S-4CPF; 9-(4-carboxy-2-sulfophenyl)-2,3,7-trihydroxy-6-fluorone (the compound of formula [B], wherein $R_1=SO_3H$, $R_2=CO_2H$, hereinafter described as 2S-4CPF)

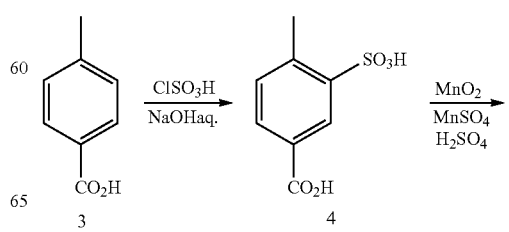

-continued

[Structure: CHO, SO₃H, CO₂H substituted benzene + AcO, OAc, AcO, OAc substituted benzene]

→ (H₂SO₄, EtOHaq., KPS)

5

[Structure of compound 6: fluorescein-type xanthene with HO, HO, OH groups and phenyl-SO₃H, CO₂H substituent]

6 p-toluic acid (3) (1.0 g, 7.3 mmol, produced by Wako Pure Chemical Industries, Ltd.) was heated at 90° C. for 4 hours in the presence of chlorosulfuric acid (2.56 g, 21.6 mmol), and reacted. After completion of the reaction, the resultant reaction solution was poured into ice and neutralized with aqueous sodium hydroxide solution, and the reaction solution was vacuum distilled. Then, the resultant residue was purified with a reversed-phase column (eluent: $H_2O \rightarrow 20\%$ MeOHaq.) to obtain a compound (4) (yield: 1.60 g, yield: quant.).

$^1$H-NMR (DMSO-$d_6$) δ (ppm): 2.55 (3H, s), 7.23 (1H, d) 7.74 d), 8.29 (1H, s).

MALDI TOF Mass (nega: 215).

Then, using manganese oxide-manganese sulfate (82 mg, 1.15 mmol) as an oxidizing agent, the compound (4) (50 mg, 0.23 mmol) was reacted in 60% sulfuric acid at 110° C. for 4 hours. After completion of the reaction, the resultant reaction solution was subjected to filtration through Celite to obtain a filtrate including the compound (5). To the filtrate obtained, 1,3,4-triacetoxy benzene (116 mg, 0.46 mmol) was added, and subjected to Friedel-Crafts acylation in the presence of concentrated sulfuric acid/50% ethanol at 80° C. After confirming the disappearance of the starting materials by HPLC, further by adding potassium persulfate (62 mg, 0.23 mmol), oxidative ring closure reaction was carried out at 80° C. After completion of the reaction, the reaction mixture was allowed to stand overnight. Precipitated crystals were washed with cooled 50% ethanol to obtain the objective 2S-4CPF (6) (yield: 16 mg, yield: 16%).

$^1$H-NMR (DMSO-$d_6$) δ (ppm): 6.60 (2H, s), 7.11 (1H, d), 7.15 (2H, s), 7.73 (1H, d), 8.26 (1H, s).

MALDI TOF Mass (posi: 444).

Example 3

[Preparation of Reagent Solution]
(R-1) First Reagent Solution:
A 100 mM tricine buffer solution (pH 8.0) containing 0.5% (w/v) polyvinylpyrrolidone (K-90) (produced by Wako Pure Chemical Industries, Ltd.) was used as the first reagent solution.

(R-2) Second Reagent Solution:
A 100 mM tricine buffer solution (pH 8.0) containing 1 mM 4S-SPF synthesized in Example 1 or 1 mM 2S-4CPF synthesized in Example 2 was used as the second reagent solution.

[Sample]
Aqueous ferrous ammonium sulfate solution (containing 200 μg/dL iron) was prepared and used as a sample.

[Measurement of Absorbance]
For the above-described sample, the measurement of absorbance was carried out using the reagent solution described above, and using JEOL BM6050 automatic analyzer (manufactured by JEOL Co., Ltd.) by the following measurement conditions. In addition, when the measurement of reagent blank, measurement was carried out in the same manner using physiological saline instead of the sample.

[Measurement Conditions]
Analysis method/Reaction time: [EPA] [10]
Measurement point: [44], [47]-[95], [98].
Wavelength (secondary/dominant): [694] [596]
Sample volume: 8 μL (2 times dilution at measurement)
R-1: 60 μL
R-2: 20 μL
Measurement temperature: 37° C.

It should be noted that the concentration of 4S-SPF or 2S-4CPF at the time of measurement was 0.23 mM.

Figure 2:
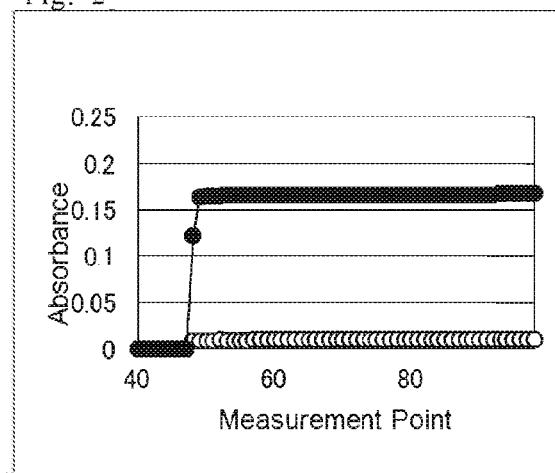
FIG. 2 is the measurement results of absorbance carried out using 9-(4-carboxy-2-sulfophenyl)-2,3,7-trihydroxy-6-fluorone (2S-4CPF) as a chelate color former, obtained in Example 3.

[Results]
The measurement result obtained by use of 4S-SPF was shown in FIG. 1, and the measurement result obtained by use of 2S-4CPF was shown in FIG. 2, showing with respect to aqueous iron solution (-●-) and physiological saline (-○-), respectively.

Comparative Example 1

[Preparation of Reagent Solution]
(R-1) First Reagent Solution:
A 100 mM tricine buffer solution (pH 8.0) containing 0.5% (w/v) polyvinylpyrrolidone (K-90) was used as the first reagent solution.

(R-2) Second Reagent Solution:
A 100 mM tricine buffer solution (pH 8.0) containing 1 mM CPF was used as the second reagent solution. The CPF was synthesized according to the method described in the Mitsuru Hoshino et al., Yakugaku Zassi, 2011, vol. 131, No. 7, p. 1095-1101 (Non-Patent Literature 1), and used.

[Sample]
Aqueous ferrous ammonium sulfate solution (containing 200 μg/dL iron) prepared and used as a sample.

[Measurement of Absorbance]
For the above-described sample, the measurement of absorbance was carried out using the reagent solution described above and using JEOL BM6050 automatic analyzer (manufactured by JEOL Co., Ltd.) by the same measurement conditions as performed in Example 3. In addition, for the measurement of reagent blank, measurement was carried out in the same manner using physiological saline instead of the sample.

It should be noted that, the concentration of CPF at the time of measurement was 0.23 mM.

Figure 3:
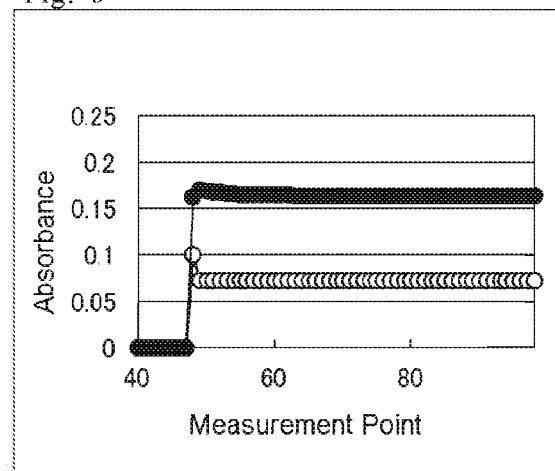
FIG. 3 is the measurement results of absorbance carried out using the conventionally used CPF as a chelate color former, obtained in Comparative Example 1.

[Results]
The result was shown in FIG. 3 with respect to aqueous iron solution (-●-) and saline (-○-).

As is clear from the results of FIG. 1 to FIG. 3, when CPF was used as a chelate color former, the blank value was high (FIG. 3), however, when the 4S-SPF (FIG. 1) and 2S-4CPF (FIG. 2) which were both the compound of the present invention were used as the chelate color former, respective blank values were suppressed lower.

In addition, when the CPF was used as a chelate color former, color fading after color development was observed (FIG. 3), however, when the 4S-SPF (FIG. 1) and 2S-4CPF (FIG. 2) were used as a chelate color former, color fading was not confirmed, and it turned out that the color development was stable.

From the results stated above, it turned out that when the compound of the present invention was used as a chelate color former, the blank value was suppressed, and highly-sensitive measurement of iron concentration can be performed.

Example 4

[Preparation of Reagent Solution]
(R-1) First Reagent Solution:
A 10 mM glycine buffer solution (pH 3.2) containing 0.5% (w/v) polyvinylpyrrolidone (K-90) (produced by Wako Pure Chemical Industries, Ltd.) was used as the first reagent solution.
(R-2) Second Reagent Solution:
A 100 mM tricine buffer solution (pH 9.0) containing 1 mM 4S-SPF which was synthesized in Example 1 or 1 mM 2S-4CPF which was synthesized in Example 2 was used as the second reagent solution.
[Sample]
The sample used was same as used in Example 3.
[Measurement of Absorbance]
For the above-described sample, the measurement of absorbance was carried out using the reagent solution described above and using JEOL BM6050 automatic analyzer (manufactured by JEOL Co., Ltd.) by the same measurement conditions as performed in Example 3.
It should be noted that, the concentration of 4S-SPF or 2S-4CPF at the time of measurement was 0.23 mM.
[Results]
The measurement results obtained by use of 4S-SPF was shown in FIG. 4, and the measurement results obtained by use of 2S-4CPF was shown in FIG. 5, showing with respect to aqueous iron solution (-●-) and saline (-○-), respectively.

Comparative Example 2

[Preparation of Reagent Solution]
(R-1) First Reagent Solution:
A 10 mM glycine buffer solution (pH 3.2) containing 0.5% (w/v) polyvinylpyrrolidone (K-90) was used as the first reagent solution.
(R-2) Second Reagent Solution:
A 100 mM tricine buffer solution (pH 9.0) containing 1 mM CPF was used as the second reagent solution. CPF was synthesized according to the method described in the Mitsuru Hoshino et al., Yakugaku Zassi, 2011, vol. 131, No. 7, p. 1095-1101 (Non-Patent Literature 1), and used.
[Sample]
The sample used was the same as used in Example 4.
[Measurement of Absorbance]
For the above-described sample, the measurement of absorbance was carried out using the reagent solution described above and using JEOL BM6050 automatic analyzer (manufactured by JEOL Co., Ltd.) by the same measurement conditions as performed in Example 4.
It should be noted that, the concentration of the CPF at the time of measurement was 0.23

Figure 6:
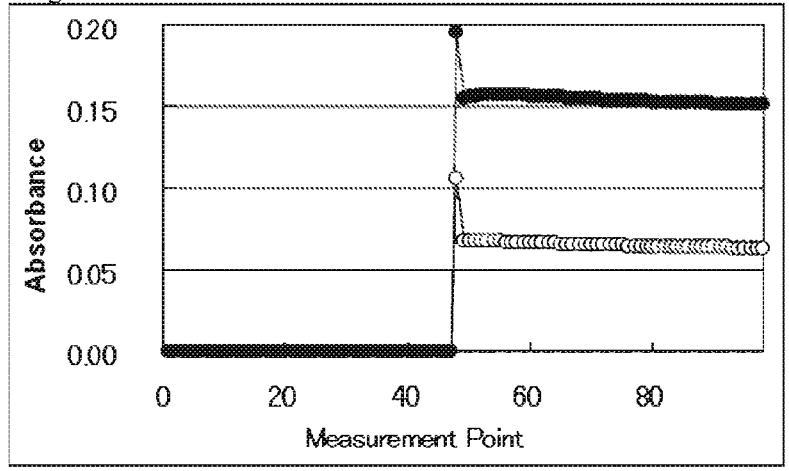
FIG. 6 is the measurement results of absorbance carried out using the conventionally used CPF as a chelate color former, obtained in Comparative Example 2.

[Results]
The result was shown in FIG. 6 with respect to aqueous iron solution (-●-) and saline (-○-).

Figure 4:
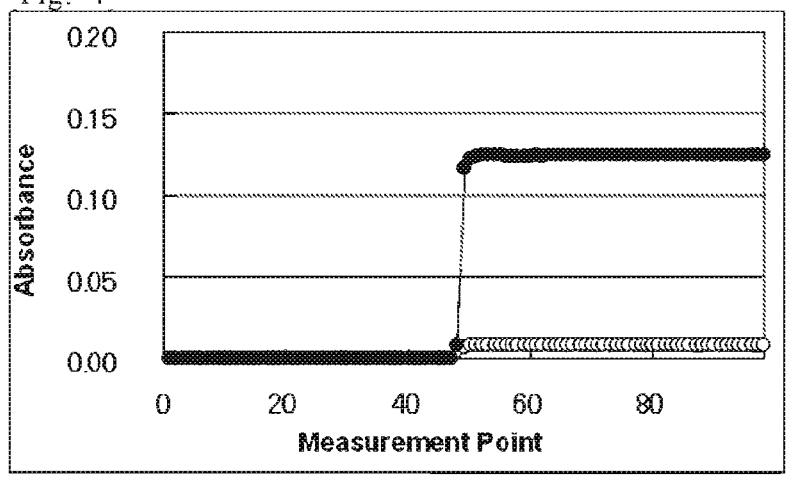
FIG. 4 is the measurement results of absorbance carried out using 9-(2,4-disulfophenyl)-2,3,7-trihydroxy-6-fluorone (4S-SPF) as a chelate color former, obtained in Example 4.
Figure 5:
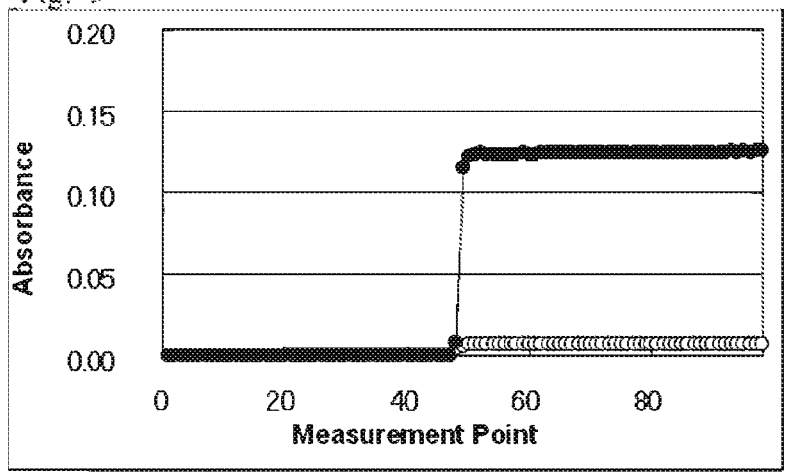
FIG. 5 is the measurement results of absorbance carried out using 9-(4-carboxy-2-sulfophenyl)-2,3,7-trihydroxy-6-fluorone (2S-4CPF) as a chelate color former, obtained in Example 4.

As is clear from the results of FIG. 4 to FIG. 6, when CPF was used as a chelate color former, the blank value was high (FIG. 6), however, when the 4S-SPF (FIG. 4) and 2S-4CPF (FIG. 5) were used as the chelate color former, respective blank values were suppressed lower.

In addition, when the CPF was used as a chelate color former, color fading after color development was observed (FIG. 6), however, when the 4S-SPF (FIG. 4) and 2S-4CPF (FIG. 5) were used as a chelate color former, color fading was not observed, and it turned out that the color development was stable.

From the results stated above, it turned out that when the compound of the present invention was used as a chelate color former, the blank value was suppressed, and more sensitive measurement of iron concentration can be performed.

In addition, in Example 4 and Comparative Example 2, the measurement was carried out by use of the first reagent solution of pH 3.2. On the occasion of measuring serum iron concentration, although the first reagent solution adjusted to pH 3 to pH 7 was used, as is clear from the comparison of FIG. 3 with FIG. 6, when the iron concentration was measured using the conventional iron-chelating color former CPF under the condition of serum iron concentration measurement, fading after color development was remarkable. On the other hand, as is clear from comparison of FIG. 1 with FIG. 4 and comparison of FIG. 2 with FIG. 5, when 4S-SPF and 2S-4CPF which were the compounds of the present invention were used as a chelate color former, even when the measurement was carried out under the condition of serum iron concentration measurement, fading after color development was not observed. From this fact, it turned out that the compound of the present invention is particularly excellent as a chelate color former to be used for the measurement of serum iron concentration, and by using the compound of the present invention as a chelate color former, the measurement of serum iron concentration can be performed with high sensitivity.

Example 5

[Preparation of Reagent Solution]
(R-1) First Reagent Solution:
The same first reagent solution as used in Example 3 was used.
(R-2) Second Reagent Solution:
The same second reagent solution (containing 4S-SPF or 2S-4CPF) as used in Example 3 was used.
[Sample]
The same sample as used in Example 3 was used.
[Measurement of Absorbance]
For the above-described sample, the measurement of absorbance was carried out using the reagent solution described above and using a Hitachi U-3900H Spectrophotometer (manufactured by Hitachi High-Technologies Co., Ltd.) by the following measurement conditions. In addition, for the measurement of reagent blank, physiological saline was used.
(Measurement Conditions)
Reaction time: 5 minutes-5 minutes
Measurement wavelength: 500 nm to 700 nm
Sample volume: 160 μL R-1: 2400 μL
R-2: 800 μL
Measurement temperature: 37° C.

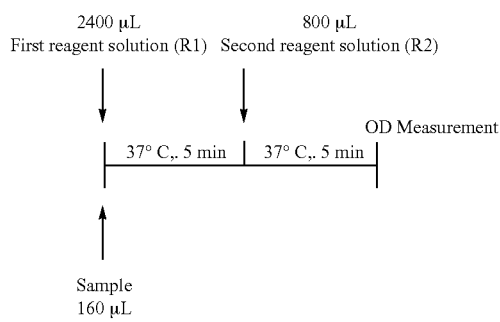

It should be noted that the concentration of 4S-SPF or 2S-4CPF at the time of measurement was 0.24 mM.
[Results]

Figure 7:
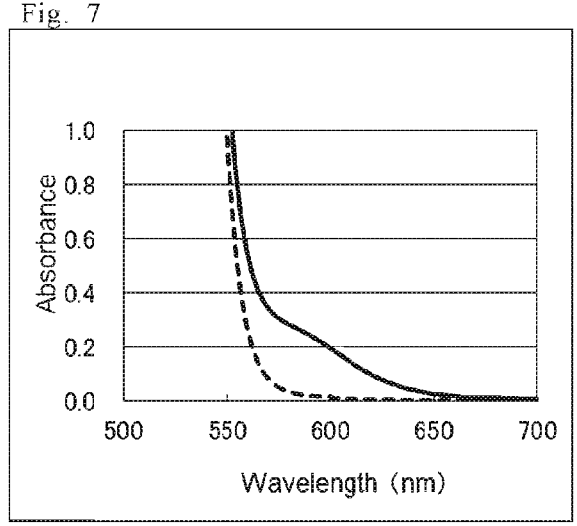
FIG. 7 is an absorption curve at 500 nm to 700 nm obtained by carrying out measurements using 4S-SPF as a chelate color former, obtained in Example 5.
Figure 8:
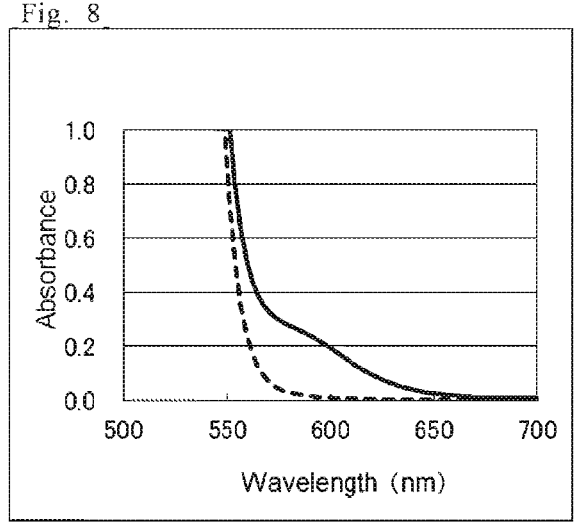
FIG. 8 is an absorption curve at 500 nm to 700 nm obtained by carrying out measurements using 2S-4CPF as a chelate color former, obtained in Example 5.

Absorption curve obtained by the measurement using 4S-SPF was shown in FIG. 7, and absorption curve obtained by measurement using 2S-4CPF was shown in FIG. 8. In addition, in FIG. 7 and FIG. 8, the result obtained using aqueous iron solution as a sample was shown by a solid line (-), and the result obtained using physiological saline as a sample was shown by a dotted line ( - - - ), respectively.

Comparative Example 3

[Preparation of Reagent Solution]
(R-1) First Reagent Solution:

The same first reagent solution as used in Comparative Example 1 was used.
(R-2) Second Reagent Solution:

The same second reagent solution (containing CPF) as used in Comparative Example 1 was used.
[Sample]

The same sample as used in Comparative Example 1 was used.
[Measurement of Absorbance]

For the above-described sample, the measurement of absorbance was carried out using the reagent solution described above and using a Hitachi U-3900H Spectrophotometer by the same measurement conditions as carried out in Example 5.

It should be noted that, the concentration of CPF at the time of measurement was 0.24 mM.
[Results]

Figure 9:
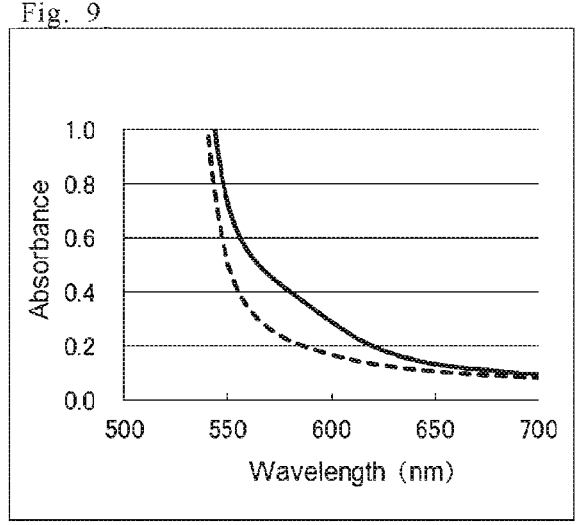
FIG. 9 is an absorption curve at 500 nm to 700 nm obtained by carrying out measurements using the conventionally used CPF as a chelate color former, obtained in Comparative Example 3.

Absorption curve obtained was shown in FIG. 9. In FIG. 9, the result obtained using aqueous iron solution as a sample was shown by a solid line (-), and the result obtained using physiological saline as a sample was shown by a dotted line ( - - - ), respectively.

As is clear from the results of FIG. 7 to FIG. 9, when CPF was used as a chelate color former, absorbance of the blank was high at 590 nm to 600 nm which was an absorption wavelength of iron-chelate complex (FIG. 9), however when 4S-SPF (FIG. 7) and 2S-4CPF (FIG. 8) were used as a chelate color former, absorbance of the blank was suppressed lower even at 590 nm to 600 nm.

From the results described above, it turned out that when the compound of the present invention was used as a chelate color former, the blank value was suppressed, and the measurement of iron concentration can be performed with high sensitivity.

Example 6

[Preparation of Reagent Solution]
(R-1) First Reagent Solution:

A 10 mM glycine buffer solution (pH 3.2) containing 0.5% polyvinylpyrrolidone (K-90) was used as a first reagent solution.
(R-2) Second Reagent Solution:

A 100 mM tricine buffer solution (pH 9.0) containing 1 mM 4S-SPF which was synthesized in Example 1 was used as a second reagent solution.
[Sample]

The human serum was used.
[Measurement of Absorbance]

For the above-described sample, using the reagent solution described above, and using a Hitachi 7170S Automatic Analyzer (manufactured by Hitachi High-Technologies Co., Ltd.), measurement of absorbance was carried out under the following conditions, and absorbance difference in 5 minutes ($\Delta$OD) from 16 points (5 minutes after the start of reaction) to final 34 points (10 minutes after the start of reaction) was determined.

By applying the obtained $\Delta$OD to a standard curve which indicates a relationship between iron concentration and absorbance obtained by carrying out the measurement in the same manner using Multi calibrator A (produced by Wako Pure Chemical Industries, Ltd., containing 200 μg/dL of iron) as a sample of known iron concentration instead of the serum sample in advance, the iron concentration in each sample was measured.

It should be noted that, for the measurement of reagent blank, physiological saline was used.
(Measurement Conditions)

Analysis method/Reaction time: [2 point end][10]
Measurement point: [16]-[34]
Wavelength (secondary/dominant): [700][600]
Sample volume: 10 μL
R-1: 150 μL
R-2: 50 μL
Measurement temperature: 37° C.

The pH of the solution at the time of mixing the first reagent solution and the second reagent solution was pH 8.0. In addition, the concentration of 4S-SPF at the time of measurement was 0.23 mM.

In addition, by using L type Wako Fe.N (produced by Wako Pure Chemical Industries, Ltd.) which is a kit for measurement of iron concentration according to the direct method using bathophenanthroline of a conventional iron-chelate color former, and according to the standard procedure described in the actual product manual of kit, the measurement of iron concentration in the same sample as described above was measured.
[Results]

A correlation diagram between the measurement value of the serum iron concentration obtained by using a reagent with the use of compound of the present invention (4S-SPF) and the measurement value of the serum iron concentration obtained by using a reagent (L type Wako Fe.N) with the use of conventional bathophenanthroline was shown in FIG. 10.

The regression line equation and the correlation coefficient obtained by performing regression analysis of the results of FIG. 10 were as follows.

y=0.988x+0.3

R=0.999

As is clear from the above results, the measurement value of the serum iron concentration obtained by using a reagent with the use of compound of the present invention (4S-SPF) showed a good correlation with the measurement value of the serum iron concentration obtained by using a reagent (L type Wako Fe.N) with the use of conventional bathophenanthroline.

From this fact, it turned out that the concentration of iron in the serum can be measured quantitatively using the compound of the present invention as a chelate color former.

INDUSTRIAL APPLICABILITY

The present invention provides a method for measuring iron concentration with high accuracy and high sensitivity using a novel compound of the present invention represented by the formula [1] and the salt thereof as a chelate color former, and a reagent for measuring iron concentration and an kit for measuring iron concentration including the compound as a chelate color former and as a constituent.

REFERENCE SIGNS LIST

In FIG. 1, FIG. 2, FIG. 3, FIG. 4, FIG. 5 and FIG. 6, -●- represents the result obtained by using an aqueous iron solution as a sample, and -○- represents the result obtained by using physiological saline as a sample, respectively.

In FIG. 7, FIG. 8 and FIG. 9, the solid line (-) represents the result obtained by using an aqueous iron solution as a sample, and the dotted line ( - - - ) represents the result obtained by using physiological saline as a sample, respectively.

The invention claimed is:

1. A method for measuring iron concentration in a sample, comprising:

contacting iron in the sample with a compound represented by the following formula [1] or a salt thereof as a chelate color former; and measuring iron concentration in the sample on the basis of a degree of resulting color development,

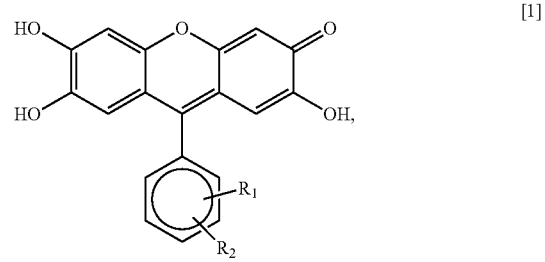

[1]

wherein $R_1$ and $R_2$ each independently represent —$SO_3H$ or —$CO_2H$.

2. The method according to claim 1, wherein the compound represented by the formula [1] or the salt thereof is the compound represented by the following formula [2] or the salt thereof

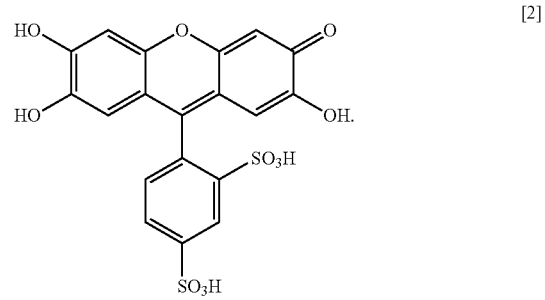 [SMILES: O=c1cc2oc3cc(O)c(O)cc3c(-c3ccc(S(=O)(=O)O)cc3S(=O)(=O)O)c-2cc1O]

[2]

* * * * *